: US 9,334,218 B2

United States Patent
Wang et al.

(10) Patent No.: US 9,334,218 B2
(45) Date of Patent: May 10, 2016

(54) PROCESS FOR MAKING PHENOL AND/OR CYCLOHEXANONE

(71) Applicant: ExxonMobil Chemical Patents Inc., Baytown, TX (US)

(72) Inventors: Kun Wang, Bridgewater, NJ (US); Roberto Garcia, Easton, PA (US); Terry E. Helton, Montgomery, TX (US); Hari Nair, Houston, TX (US); Charles Morris Smith, Princeton, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/443,175

(22) PCT Filed: Dec. 6, 2013

(86) PCT No.: PCT/US2013/073707
§ 371 (c)(1),
(2) Date: May 15, 2015

(87) PCT Pub. No.: WO2014/099426
PCT Pub. Date: Jun. 26, 2014

(65) Prior Publication Data
US 2015/0291495 A1 Oct. 15, 2015

Related U.S. Application Data

(60) Provisional application No. 61/740,272, filed on Dec. 20, 2012.

(30) Foreign Application Priority Data

Mar. 19, 2013 (EP) .................................... 13159862

(51) Int. Cl.
C07C 45/53 (2006.01)
C07C 37/08 (2006.01)
C07C 2/74 (2006.01)

(52) U.S. Cl.
CPC ................. *C07C 45/53* (2013.01); *C07C 37/08* (2013.01); *C07C 2101/14* (2013.01)

(58) Field of Classification Search
CPC ............ C07C 45/53; C07C 37/08; C07C 2/66
USPC .................................. 568/376, 798; 585/467
See application file for complete search history.

(56) References Cited

U.S. PATENT DOCUMENTS

| 3,959,381 A | 5/1976 | Arkell et al. |
| 4,021,490 A | 5/1977 | Hudson |
| 6,037,513 A | 3/2000 | Chang et al. |

FOREIGN PATENT DOCUMENTS

| JP | 2007-099745 | 4/2007 |
| JP | 2007-099746 | 4/2007 |
| WO | 2009/010224 | 1/2009 |
| WO | WO 2012/067711 | 5/2012 |
| WO | WO 2012/145030 | 10/2012 |

*Primary Examiner* — Sikarl Witherspoon
(74) *Attorney, Agent, or Firm* — Stephen A. Baehl; Siwen Chen

(57) ABSTRACT

A cleavage process for making phenol and/or cyclohexanone, the process comprising: (A) providing a feed comprising cyclohexylbenzene hydroperoxide; (B) contacting the feed with a catalyst under cleavage reaction conditions effective to produce a cleavage effluent comprising phenol and cyclohexanone, the catalyst having a collidine uptake of at least 20 µmol per gram of the catalyst and comprising an aluminosilicate molecular sieve of the FAU-type, an oxide binder, and a clay.

23 Claims, 1 Drawing Sheet

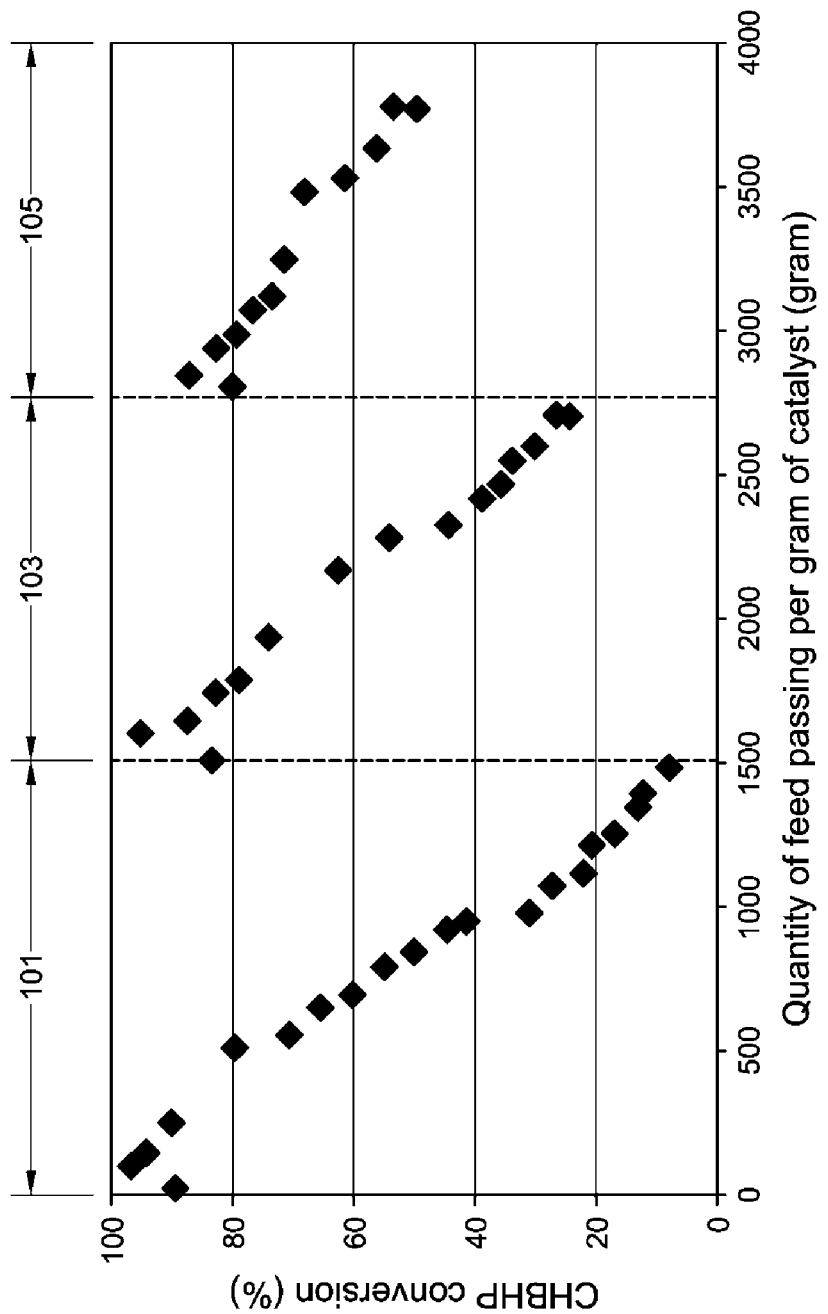

PROCESS FOR MAKING PHENOL AND/OR CYCLOHEXANONE

PRIORITY CLAIM TO RELATED APPLICATIONS

This application is a National Stage Application of International Application No. PCT/US2013/073707 filed Dec. 6, 2013, which claims priority to U.S. Provisional Application Ser. No. 61/740,272 filed Dec. 20, 2012, and European Application No. 13159862.5 filed Mar. 19, 2013, the disclosures of which are fully incorporated herein by their reference.

FIELD

The present invention relates to a process for producing phenol and/or cyclohexanone. In particular, the present disclosure relates to a process for producing phenol and/or cyclohexanone comprising a step of cleaving cyclohexylbenzene hydroperoxide in the presence of a cleavage catalyst. The present invention is useful, e.g., in producing phenol and cyclohexanone starting from the hydroalkylation of benzene.

BACKGROUND

Phenol and cyclohexanone are important products in the chemical industry and are useful in, for example, the production of phenolic resins, bisphenol A, ε-caprolactam, adipic acid, plasticizers and nylon polymers.

Currently, a common route for the production of phenol is the Hock process via cumene. This is a three-step process in which the first step involves alkylation of benzene with propylene in the presence of an acidic catalyst to produce cumene. The second step is oxidation, preferably aerobic oxidation, of cumene to the corresponding cumene hydroperoxide. The third step is the cleavage of the cumene hydroperoxide generally in the presence of sulfuric acid catalyst into equimolar amounts of phenol and acetone, a co-product.

It is known that phenol and cyclohexanone can be co-produced by a variation of the Hock process in which cyclohexylbenzene is oxidized to obtain cyclohexylbenzene hydroperoxide and the hydroperoxide is decomposed in the presence of an acid catalyst to the desired phenol and cyclohexanone. Although various methods are available for the production of cyclohexylbenzene, a preferred route is disclosed in U.S. Pat. No. 6,037,513, which includes a step of contacting benzene with hydrogen in the presence of a bifunctional catalyst comprising a molecular sieve of the MCM-22 family and at least one hydrogenation metal selected from palladium, ruthenium, nickel, cobalt and mixtures thereof. This reference also discloses that the resultant cyclohexylbenzene can be oxidized to the corresponding hydroperoxide which is then decomposed to the desired phenol and cyclohexanone co-product.

In producing phenol from cyclohexylbenzene, the problems are different. Firstly, oxidation of cyclohexylbenzene to cyclohexylbenzene hydroperoxide is much more difficult than oxidation of cumene and is desirably conducted at elevated temperatures and in the presence of a catalyst, such as N-hydroxyphthalimide (NHPI). In addition, the cleavage chemistry for cyclohexylbenzene hydroperoxide is much more complicated than that for cumene hydroperoxide, particularly since more routes for by-product formation exist with cyclohexylbenzene hydroperoxide cleavage, especially if sulfuric acid is used as the cleavage catalyst. Moreover, cyclohexanone is much more prone to acid-catalyzed aldol condensation reactions than acetone so that significant yield loss is possible unless the cyclohexylbenzene hydroperoxide cleavage is closely controlled.

There are other disadvantages of using sulfuric acid for cyclohexylbenzene hydroperoxide cleavage: 1) sulfuric acid is corrosive, especially in the presence of water, requiring expensive materials for reactor construction; 2) sulfuric acid needs to be neutralized before product separation and distillation, which requires additional chemicals such as phenate, caustics, or organic amines; and 3) the salt generated from neutralization of the sulfuric acid requires separation and disposal and the waste water needs to be treated. Therefore, there are strong incentives to replace sulfuric acid with a heterogeneous cleavage catalyst that eliminates these drawbacks.

SUMMARY

According to the present disclosure, it has now been found that, although a number of solid acids, including aluminosilicate molecular sieves and catalysts based on them, have activity for the conversion of cyclohexylbenzene hydroperoxide into phenol and cyclohexanone, high-strength catalyst particles comprising large pore molecular sieves of the FAU-type, an oxide binder, and a clay, especially those having a spherical or spheroidal shape, such as those suitable for fluid catalytic cracking, exhibit a unique combination of high activity, high selectivity and high durability. Furthermore, we have surprisingly found that even the equilibrium FCC catalysts, which contain both fresh and varying age of spent catalyst particles, as well as metal contaminants such as V, Ni, and Fe, can effectively catalyze the cleavage of cyclohexylbenzene hydroperoxide into phenol and cyclohexanone with good selectivity. Such catalysts can be conveniently regenerated and used either in a slurry phase reactor or a fixed-bed reactor.

The present disclosure relates to a process for making phenol and/or cyclohexanone, the process comprising:

(A) providing a feed comprising cyclohexylbenzene hydroperoxide;

(B) contacting the feed with a catalyst under cleavage reaction conditions effective to produce a cleavage effluent comprising phenol and cyclohexanone, the catalyst having a collidine uptake of at least 20 μmol per gram of the catalyst and comprising (i) an aluminosilicate molecular sieve of the FAU-type; (ii) an oxide binder; and (iii) a clay.

The catalyst may comprise the molecular sieve of the FAU-type in a range from 20 wt % to 60 wt %, the oxide binder in a range from 10 wt % to 40 wt %, and the clay in a range from 5 wt % to 30 wt %, all percentages based on the total weight of the catalyst.

For example, the catalyst may comprise a FCC catalyst, such as a spent FCC catalyst.

The catalyst may meet at least one of the following requirements: (r1) comprising vanadium in a range from 0.05 wt % to 1.0 wt %, (r2) comprising nickel in a range from 0.01 wt % to 0.5 wt %, and (r3) comprising iron in a range from 0.05 wt % to 1.0 wt %, where all percentages are based on the total weight of the catalyst.

The catalyst may comprise a plurality of particles having an average size in a range from 20 μm to 200 μm. At least 50% of the plurality of the particles may be spheroidal and/or spherical, the percentages based on the total number of the particles.

It is to be understood that the foregoing general description and the following detailed description are merely exemplary of the invention, and are intended to provide an overview or framework to understanding the nature and character of the invention as it is claimed.

BRIEF DESCRIPTION OF THE DRAWING

FIG. 1 is a diagram showing the conversion of cyclohexylbenzene hydroperoxide as a function of the quantity of feed flowing through the catalyst on a per gram basis in a cleavage reaction in the Examples of the present disclosure.

DETAILED DESCRIPTION

In the present disclosure, a process is described as comprising at least one "step." It should be understood that each step is an action or operation that may be conducted once or multiple times in the process in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be conducted simultaneously with respect to an intermediate material resulting from treating the raw materials fed into the process at an earlier time in the first step. Preferably, the steps are performed in the order listed.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenation metal" include embodiments where one, two or more different types of the hydrogenation metals are used, unless specified to the contrary or the context clearly indicates that only one type of the hydrogenation metal is used.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question unless specified or indicated otherwise. All ranges expressed herein should include both end points as two specific embodiments unless specified or indicated to the contrary.

The terms "group," "radical," and "substituent" are used interchangeably in the present disclosure.

As used herein, the generic term "dicyclohexylbenzene" includes, in the aggregate, 1,2-dicyclohexylbenzene, 1,3-dicyclohexylbenzene, and 1,4-dicyclohexylbenzene, unless clearly specified to mean only one or two thereof. The term "cyclohexylbenzene," when used in singular form, means mono substituted cyclohexylbenzene.

As used herein, a "FCC catalyst" is a catalyst suitable for use in a commercial petroleum fluid catalytic cracking process, a "spent FCC catalyst" is a FCC catalyst that has been exposed to the reaction conditions of a petroleum fluid catalytic cracking process, and an "equilibrium FCC catalyst" is a mixture of spent FCC catalyst and fresh FCC catalyst that has not been exposed to a petroleum fluid catalytic cracking process.

As used herein, an "effluent" of a process can be a product stream of a continuous process, or a product of a batch process or semi-batch process.

In the present disclosure, the "collidine uptake" of a catalyst is measured on a TA Instruments Q5000 model TGA machine (available from TA Instruments, 159 Lukens Drive, New Castle, Del. 19720, U.S.A.) with a modified gas and vapor delivery system. A catalyst sample of 10 to 50 mg is first dried under flowing $N_2$ (90 $cm^3$/min) at 200° C. for 60 minutes or until a stable weight is achieved. Then a $N_2$ stream (90 $cm^3$/min) flowing through a reservoir of collidine (2,4,6-trimethylpyridine, held at 35° C.) and a condenser (held at 26° C.) is delivered to the sample. The partial pressure of collidine is set by the temperature of the condenser and the $N_2$ flow rate. The sparged collidine was delivered over the sample for 60 minutes, followed by 60 minutes of stripping with flowing $N_2$. The increase in sample weight indicates adsorption of collidine. Uptake is reported in µmol (i.e., micromole) collidine per gram of catalyst.

In the present disclosure, the "n-hexane uptake" of a catalyst is measured on a TA Instruments Q5000 model TGA with a modified gas and vapor delivery system. A catalyst sample of 10 to 50 mg is first dried under flowing helium (100 $cm^3$/min) at 500° C. for 30 minutes or until a stable weight is achieved. Then a helium stream (68 $cm^3$/min) flowing through a reservoir of n-hexane (held at 35° C.) and a condenser (held at 18° C.) combined with 32 $cm^3$/min helium make-up gas is delivered to the sample. The partial pressure of n-hexane is set by the temperature of the condenser and the helium flow rate through the sparger. The sparged n-hexane was delivered over the sample for 30 minutes. The increase in sample weight indicated adsorption of n-hexane. Uptake is reported in mg n-hexane per gram of catalyst.

In the present disclosure, the maximal TPAD (Temperature Programmed Ammonia Desorption) temperature of a catalyst is measured on the Mettler Thermal Gravimetrical Analysis (TGA) instrument (available from Mettler-Toledo, LLC, 1900 Polaris Parkway, Columbus, Ohio 43240, U.S.A.). A catalyst sample of 20 to 50 mg is first loaded and calcined in air at 500° C. The sample is then cooled down in air to 250° C. The gas flow is then switched to helium and the dry weight of the sample is taken when the reading is stable. Subsequently, recurrent pulses of 50 $cm^3$/min 1 wt % $NH_3$ in helium are used while maintaining a 30 $cm^3$/min continuous helium flow over the catalyst. Thus the acid sites are saturated with $NH_3$. Weakly adsorbed ammonia is purged by flowing helium. The ammonia uptake capacity is measured at 190 minutes (at 250° C.). The gas flow is then switched to 50 $cm^3$/min 1 wt % $NH_3$ in helium in addition to a 30 $cm^3$/min continuous helium flow to start TPAD under adsorption equilibrium conditions. Desorption is started using a temperature ramp of 5° C./min from 250° C. to 500° C. to generate the TPAD thermogram. A 49 point Savitzky-Golay smoothing is applied. The temperature at which the ammonia desorption rate reaches maximum is reported as the measured maximal TPAD temperature value of the catalyst.

The term "MCM-22 type material" (or "material of the MCM-22 type" or "molecular sieve of the MCM-22 type" or "MCM-22 type molecular sieve"), as used herein, includes one or more of:

molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth Edition, 2001, the entire content of which is incorporated as reference;

molecular sieves made from a common second degree building block, being a 2-dimensional tiling of such MWW framework topology unit cells, forming a monolayer of one unit cell thickness, desirably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Other molecular sieves, such as UZM-8 (described in U.S. Pat. No. 6,756,030), may be used alone or together with the MCM-22 type molecular sieves as well for the purpose of the present disclosure. Desirably, the molecular sieve is selected from (a) MCM-49; (b) MCM-56; and (c) isotypes of MCM-49 and MCM-56, such as ITQ-2.

Described herein is a process for producing phenol by cleavage of cyclohexylbenzene hydroperoxide in the presence of a catalyst having a collidine uptake of at least 20 μmol per gram of the catalyst and comprising (i) an aluminosilicate molecular sieve of the FAU-type; (ii) an oxide binder; and (iii) a clay. The use of such a catalyst allows high conversion of cyclohexylbenzene hydroperoxide combined with high selectivity to phenol and cyclohexanone without the disadvantages inherent in the use of homogeneous catalysts, such as sulfuric acid. The catalyst also exhibits a long durability suitable for recirculating slurry reactions.

The present cleavage process can advantageously form part of an integrated process for producing phenol and cyclohexanone from benzene, in which benzene is converted to cyclohexylbenzene, cyclohexylbenzene is then oxidized to cyclohexylbenzene hydroperoxide and cyclohexylbenzene hydroperoxide is then cleaved to produce phenol and cyclohexanone. The present process will therefore now be more particularly described with reference to this specific example. One having ordinary skill in the art should readily understand that, in the light of teachings of the present disclosure, one may use the cleavage process for cyclohexylbenzene hydroperoxide produced by other means.

Production of Cyclohexylbenzene

In the integrated process for producing phenol and cyclohexanone from benzene, the benzene is initially converted to cyclohexylbenzene by any conventional technique, including alkylation of benzene with cyclohexene in the presence of an acid catalyst, such as zeolite beta or an MCM-22 type molecular sieve, or by oxidative coupling of benzene to make biphenyl followed by hydrogenation of the biphenyl. However, in practice, the cyclohexylbenzene is desirably produced by contacting the benzene with hydrogen under hydroalkylation conditions in the presence of a hydroalkylation catalyst whereby the benzene undergoes the following Reaction-1 to produce cyclohexylbenzene (CHB):

(Reaction-1)

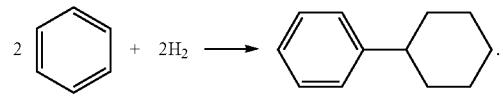

For an example of hydroalkylation of benzene in the presence of hydrogen for the production of cyclohexylbenzene, see U.S. Pat. Nos. 6,730,625 and 7,579,511, which are incorporated by reference. Also, see International Publications WO2009/131769 or WO2009/128984, directed to catalytic hydroalkylation of benzene in the presence of hydrogen for the production of cyclohexylbenzene. The hydroalkylation is advantageously conducted in a reactor equipped with a fluid distributing device described above.

The catalyst employed in the hydroalkylation reaction is a bifunctional catalyst comprising a molecular sieve of the MCM-22 type and a hydrogenation metal, described above.

Any known hydrogenation metal may be employed in the hydroalkylation catalyst, although suitable metals include palladium, ruthenium, nickel, zinc, tin, and cobalt, with palladium being particularly advantageous. Desirably, the amount of hydrogenation metal present in the catalyst is from 0.05 wt % to 10 wt %, such as from 0.10 wt % to 5 wt %, of the catalyst.

Suitable binder materials include synthetic or naturally occurring substances as well as inorganic materials such as clay, silica, and/or metal oxides.

Although the hydroalkylation reaction is highly selective towards cyclohexylbenzene, the effluent from the hydroalkylation reaction may contain some dialkylated products, as well as unreacted benzene and the desired monoalkylated species. The unreacted benzene may be recovered by distillation and recycled to the reactor. The lower effluent from the benzene distillation is further distilled to separate the mono-cyclohexylbenzene product from any dicyclohexylbenzene and other heavies. Depending on the quantity of dicyclohexylbenzene present in the reaction effluent, it may be desirable to either (a) transalkylate the dicyclohexylbenzene with additional benzene or (b) dealkylate the dicyclohexylbenzene to maximize the production of the desired monoalkylated species.

Transalkylation with additional benzene is desirably effected in a transalkylation reactor, separate from the hydroalkylation reactor, over a suitable transalkylation catalyst, such as a molecular sieve of the MCM-22 type, zeolite beta, MCM-68 (see U.S. Pat. No. 6,014,018), zeolite Y, zeolite USY, and mordenite. The transalkylation reaction is desirably conducted under at least partial liquid phase conditions, which suitably include a temperature of 100° C. to 300° C., a pressure of 800 kPa to 3500 kPa, a weight hourly space velocity of 1 hr$^{-1}$ to 10 hr$^{-1}$ on total feed, and a benzene/dicyclohexylbenzene weight ratio of 1:1 to 5:1.

Oxidation of Cyclohexylbenzene

After removal of the unreacted benzene and the polyalkylated benzenes and other heavy species, the cyclohexylbenzene is fed to the oxidation reaction.

As discussed above, the process includes oxidizing at least a portion of a feed comprising cyclohexylbenzene to produce an oxidation composition comprising cyclohexyl-1-phenyl-1-hydroperoxide. As used herein, "oxidizing" means causing an oxidation reaction to occur.

Regardless of the source or sources, a feed comprising cyclohexylbenzene can contain at least 10 wt %, or at least 25 wt %, or at least 50 wt %, or at least 65 wt %, or at least 75 wt %, or at least 95 wt %, or at least 99 wt % cyclohexylbenzene. The feed may contain another component. For example, the feed comprising cyclohexylbenzene may contain at least 1 ppm, and no greater than 1 wt % bicyclohexane, or at least 10 ppm, and no greater than 8000 ppm bicyclohexane. It may contain at least 1 ppm, and no greater than 1 wt % biphenyl, or at least 10 ppm and no greater than 8000 ppm biphenyl. It may contain at least 1 ppm and no greater than 2.0 wt % methylcyclopentylbenzene, or at least 10 ppm and no greater than 1 wt % methylcyclopentylbenzene as any isomer: 1-phenyl-1-methylcyclopentane, 1-phenyl-2-methylcyclopentane, and 1-phenyl-3-methylcyclopentane. There may be other components present, though desirably of low concentration, say, no greater than 1000 ppm, or no greater than 100 ppm of phenol, olefins or alkylene benzenes such as cyclohexenyl benzene, individually or in any combination. The feed comprising cyclohexylbenzene to which oxygen is introduced to cause an oxidation reaction may contain cyclohexylbenzene, any other one component, or any combination of the other components just noted in the proportions for each, or in combination just noted.

Oxidation may be accomplished by contacting an oxygen-containing gas, such as air or various derivatives of air, with the feed comprising cyclohexylbenzene.

The oxidation may be conducted in the absence or presence of a catalyst. Suitable oxidation catalysts include N-hydroxy substituted cyclic imides (e.g., N-hydroxyphthalimide (NHPI)) described in U.S. Pat. No. 6,720,462, which is incorporated herein by reference for this purpose.

Exemplary suitable oxidation conditions include a temperature from 70° C. to 200° C., such as 90° C. to 130° C., and a pressure of 50 kPa to 10,000 kPa. A basic buffering agent may be added to react with acidic by-products that may form during the oxidation. In addition, an aqueous phase may be introduced. The reaction may take place in a batch or continuous flow fashion.

Desirably, the product of the oxidation of a feed comprising cyclohexylbenzene, i.e., the oxidation composition, contains at least 5 wt %, such as at least 10 wt %, for example, at least 15 wt %, or at least 20 wt % cyclohexyl-1-phenyl-1-hydroperoxide, based upon the total weight of the oxidation composition. In other manifestations, the oxidation composition contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation composition. The oxidation composition may further comprise imide catalyst and unreacted cyclohexylbenzene. The invention may include cyclohexylbenzene in the oxidation composition in an amount of at least 50 wt %, or at least 60 wt %, or at least 65 wt %, or at least 70 wt %, or at least 80 wt %, or at least 90 wt %, based upon total weight of the oxidation composition.

In addition, the oxidation composition may contain one or more hydroperoxides other than cyclohexyl-1-phenyl-1-hydroperoxide generated as a byproduct of the oxidation reaction of cyclohexylbenzene, or as the oxidation product of some oxidizable component other than cyclohexylbenzene that may have been contained in the cyclohexylbenzene undergoing oxidation. The reactor used for the oxidation of cyclohexylbenzene, i.e., the oxidation reactor, may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel container with a distributor inlet for the oxygen-containing stream in line. The oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. The oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner well known to those skilled in the art.

At least a portion of the oxidation composition may be subjected to a cleavage reaction, which may include all or some fraction of the oxidation composition as directly produced without undergoing any separation (e.g., some fraction resulting from diverting some amount of the oxidation composition as directly produced to another disposition, such as temporary storage). Thus, the at least a portion of the oxidation composition may have the same composition as the oxidation composition. Further, all or some of the oxidation composition, as directly produced, may undergo one or more separations, and an appropriate product of that separation (or separations), now modified in composition relative to the oxidation composition as directly produced, may provide the at least a portion of the oxidation composition subjected to the cleavage reaction.

For example, all or a fraction of the oxidation composition as directly produced may be subjected to high vacuum distillation, to generate a product enriched in unreacted cyclohexylbenzene relative to the oxidation composition, and the at least a portion of the oxidation composition as a residue concentrated in the desired cyclohexyl-1-phenyl-1-hydroperoxide that may be subjected to a cleavage reaction. Cyclohexylbenzene is essentially a diluent in the cleavage reaction and the neutralization reaction, and further is not a good solvent for most acid catalysts, particularly sulfuric acid. However, distinctive from the Hock process described earlier, it is convenient in the present disclosure that the at least a portion of the oxidation composition that will undergo the cleavage reaction be of the same composition of cyclohexylbenzene as the oxidation composition directly produced. That is to say, it is convenient that the at least a portion of the oxidation composition undergo no concentration of the hydroperoxide(s) before the acid catalyst is introduced to it, because the starting alkylbenzene cyclohexylbenzene has a significantly higher normal boiling point than the starting alkylbenzene cumene that is found in the Hock process. While within the scope of the present disclosure, any practical separation attempted to concentrate the cyclohexyl-1-phenyl-1-hydroperoxide or other hydroperoxides from cyclohexylbenzene prior to effecting the cleavage reaction likely requires very low vacuum pressure distillation equipment, and even then, likely requires very high temperatures.

Additionally or alternatively, all or a fraction of the oxidation composition, or all or a fraction of the vacuum distillation residue may be cooled to cause crystallization of the unreacted imide oxidation catalyst, which may then be separated either by filtration or by scraping from a heat exchanger surface used to effect the crystallization, and provide at least a portion of the oxidation composition reduced or free from imide oxidation catalyst that may be subjected to a cleavage reaction.

As another example, all or a fraction of the oxidation composition as produced may be subjected to water washing and then passage through an adsorbent, such as a 3 Å molecular sieve, to separate water and other adsorbable compounds, and provide at least a portion of the oxidation composition with reduced water or imide content that may be subjected to a cleavage reaction. Similarly, all or a fraction of the oxidation composition may undergo a chemically or physically based adsorption, such as passage over a bed of sodium carbonate to remove the imide oxidation catalyst (e.g., NHPI) or other adsorbable components, and provide at least a portion of the oxidation composition reduced in oxidation catalyst or other adsorbable component content that may be subjected to a cleavage reaction. Another possible separation involves contacting all or a fraction of the oxidation composition as produced with a liquid containing a base, such as an aqueous solution of an alkali metal carbonate or bicarbonate, to form an aqueous phase comprising a salt of the imide oxidation catalyst, and an organic phase reduced in imide oxidation catalyst, provided as at least a portion of the oxidation composition that may be subjected to a cleavage reaction.

Cleavage Reaction

Another step in the conversion of the cyclohexylbenzene into phenol and cyclohexanone involves the acid-catalyzed cleavage of the cyclohexyl-1-phenyl-1-hydroperoxide produced in the oxidation step. The catalyst used in the cleavage process of the present disclosure comprises (i) an aluminosilicate molecular sieve of the FAU-type; (ii) an oxide binder; and (iii) a clay. The catalyst exhibits a collidine (2,4,6-trimethypyridine) uptake of at least 20 µmol per gram of the catalyst when measured using the collidine uptake measurement protocol described above.

The solid acid catalyst may comprise the molecular sieve of the FAU-type in a range from a1 wt % to a2 wt %, the oxide binder in a range from b1 wt % to b2 wt %, and the clay in a range from c1 wt % to c2 wt %, all percentages based on the total weight of the catalyst, where a1 can be 20, 22, 24, 25, 26, 28, 30, 32, 34, 35, 36, 38, or 40; a2 can be 60, 58, 56, 55, 54, 52, 50, 48, 46, 44, 42, or 40, to the extent a1<a2; b1 can be 10, 12, 14, 15, 16, 18, 20, 22, 24, or 25, b2 can be 40, 38, 36, 35, 34, 32, 30, 28, 26, or 25, to the extent b1<b2; c1 can be 5, 6, 8, 10, 12, 14, or 15, and c2 can be 30, 28, 26, 25, 24, 22, 20, 18, or 16.

The FAU-type aluminosilicate molecular sieve contained in the catalyst may have a unit cell size in a range from UCS1 Angstroms ("Å") to UCS2 Å, where UCS1 can be 24.24, 24.26, 24.28, 24.30, 24.32, 24.34, 24.35, 24.36, 24.38, or 24.40; UCS2 can be 24.68, 24.66, 24.65, 24.64, 24.62, 24.60, 24.55, 24.50, 24.45, or 24.40, to the extent UCS1<UCS2. Unit cell size is determined by X-ray diffraction as described in ASTM D-3942. As used herein, "FAU-type molecular sieve" or "molecular sieve of the FAU-type" or "FAU molecular sieve" means a molecular sieve having a FAU-type structure as described in the *Atlas of Zeolite Framework Types*, Ch. Baerlocher et al. (6th Ed. 2007). The FAU-type aluminosilicate molecular sieve provides the acid sites on its surfaces, where the cleavage reactions take place.

Examples of the oxide binder contained in the catalyst can be $Al_2O_3$, $SiO_2$, $TiO_2$, $ZrO_2$, $MgO$, $La_2O_3$, $WO_3$, mixed oxides such as $Al_2O_3/SiO_2$, $SiO_2/MgO$, and the like.

An exemplary clay useful in the catalyst used in the process of the present disclosure is kaolin. Together with the oxide binder, the clay binds the molecular sieve particles to form the catalyst with the desired particle size, shape, strength and durability. The catalysts useful in the process having the composition described above represent an optimization of catalytic activity including, among others, hydroperoxide conversion and phenol and cyclohexanone selectivity, durability and manufacturability.

The catalyst having the above composition may have a collidine uptake as measured using the characterization protocol disclosed above in a range from CU1 to CU2, where CU1 can be 20, 25, 30, 35, 40, 45, 50, 55, 60, 70, 80, or 90; and CU2 can be 200, 190, 180, 170, 160, 150, 140, 130, 120, 110, or 100. Collidine uptake is an indication of the amount of active acid sites in the catalyst that are accessible to the hydroperoxide reactant. In general, all other conditions being equal, the higher the collidine uptake of the catalyst, the more likely the catalyst will be more active in the cleavage reaction. The inclusion of inert materials, such as some clays, can reduce the collidine uptake of the catalyst particles compared to pure FAU molecular sieve. For example, a FAU molecular sieve with a $SiO_2/Al_2O_3$ molar ratio of 5, e.g., CBV100 zeolite (available from Zeolyst International, Valley Forge, Pa., U.S.A.), which is often used in FCC catalyst formulation, has a collidine uptake capacity of about 1500 µmol/g. When the zeolite is formulated into a catalyst at 20 wt % concentration with materials with essentially zero collidine uptake such as clay, some of the accessible sites within the zeolite may be blocked, thus the measured collidine uptake may be lower than the 300 µmol/g theoretical value.

The catalysts used in the cleavage process of the present disclosure can exhibit an n-hexane uptake as measured using the characterization protocol disclosed above in a range from HU1 to HU2 mg of n-hexane per gram of the catalyst, where HU1 can be 10, 12, 14, 15, 16, 18, or 20, and HU2 can be 30, 28, 26, 25, 24, 22, or 20, to the extent HU1<HU2. The n-hexane uptake is an indicator of porosity for the catalysts. Similar to collidine uptake, the inclusion of the oxide binder and the clay can reduce the n-hexane uptake of the catalyst particles compared to pure FAU molecular sieve.

The catalyst used in the cleavage process of the present disclosure may exhibit a maximal TPAD temperature as measured using the measurement protocol disclosed above in a range from TT1° C. to TT2° C., where TT1 can be 260, 265, 270, 275, 280, 285, 290, 295 or 300; and TT2 can be 400, 395, 390, 380, 370, 360, 350, 340, 330, 320, 310, or 300, to the extent TT1<TT2. The maximal TPAD temperature is an indication of the acid site strength on the catalysts; the higher the temperature, the stronger the acid sites. The maximal temperature in TPAD reflects the strongest acidic component in the formulated catalyst, which is typically the zeolitic component; and in the catalyst used in the process of the present disclosure, the FAU-type molecular sieve.

The catalyst used in the cleavage process of the present disclosure can have a BET total surface area in a range from BS1 m$^2$/g to BS2 m$^2$/g, where BS1 can be 20, 25, 30, 35, 40, 45, 50, 55, or 60; and BS2 can be 150, 140, 130, 120, 110, 100, 90 or 80. The BET total surface area can be measured by standard method known in the art.

The cleavage catalyst may have a pore volume as measured by nitrogen (N$_2$) adsorption of greater than 0.3 cm$^3$/g, or greater than 0.4 cm$^3$/g, or greater than 0.5 cm$^3$/g. The N$_2$ adsorption can be measured by standard method known in the art.

The catalyst used in the cleavage process of the present disclosure can be derived from the catalysts suitable for petroleum fluid catalytic cracking (FCC) processes. Typical, modern FCC catalysts are particles with a bulk density of 0.80 to 0.96 g/cm$^3$ having a particle size distribution ranging from 10 to 150 μm and an average particle size of 60 to 100 μm. The desirable properties of an FCC catalyst are: good stability to high temperature and to steam; high activity; large pore sizes; good resistance to attrition; and low coke production. A modern FCC catalyst has four major components: a crystalline molecular sieve, a matrix, a binder, and a filler. The molecular sieve is the primary active component and can range from about 15 wt % to 50 wt % of the catalyst. The molecular sieve used in exemplary FCC catalysts are faujasite or Type Y catalyst comprising silica and alumina tetrahedra with each tetrahedron having either an aluminum or a silicon atom at the center and four oxygen atoms at the corners. It is a molecular sieve with a distinctive lattice structure that allows only a certain size range of hydrocarbon molecules to enter the lattice in the fluid catalytic cracking reactions. The catalytic sites in the molecular sieve are strong acids and provide most of the catalytic activity. The acidic sites are provided by the alumina tetrahedra. The aluminum atom at the center of each alumina tetrahedra is at a +3 oxidation state surrounded by four oxygen atoms at the corners which are shared by the neighboring tetrahedra. Thus, the net charge of the alumina tetrahedra is −1 which is balanced by a sodium ion during the production of the catalyst. The sodium ion is later replaced by an ammonium ion, which is decomposed to ammonia and a proton when the catalyst is subsequently calcined, resulting in the formation of Lewis and Brønsted acidic sites. The matrix component of an FCC catalyst contains amorphous alumina which also provides catalytic activity sites and in larger pores that allows entry for larger molecules than does the molecular sieve. That enables the cracking of higher-boiling, larger feedstock molecules that are not cracked by the molecular sieve. The binder and filler components provide the physical strength and integrity of the catalyst. The binder is usually silica sol and the filler is usually a clay such as kaolin. The major suppliers of FCC catalysts worldwide include Albemarle Corporation, W.R. Grace Company and BASF Catalysts.

Fresh FCC catalysts that were never used in a fluid catalytic cracking process may be used in the cleavage process of the present disclosure. In a surprising manner, it was found that even spent FCC catalysts that have been exposed to the working conditions of a FCC reactor, or mixtures of fresh and spent FCC catalysts (also known as equilibrium catalysts), may be used as well. In the process of the present disclosure, the FCC catalyst, fresh, spent, or mixture of both, may be calcined in an O$_2$-containing atmosphere (such as air) at a temperature in a range from 500° C. to 1000° C. for a period of at least Tcal minutes before contacting the cleavage feed, where Tcal can be 5, 10, 15, 30, 45, 60, 120, 180, 240, 300, 360, 420, 480, 600, 900, 1200, or even 1500. The high-temperature calcination of the FCC catalyst can eliminate the organic materials such as hydrocarbons, coking materials, and the like, entrained in the particles, thereby producing catalyst with desired catalytic activity.

Equilibrium FCC catalysts typically contain some transitional metals at a low concentration. While it is believed that transitional metals, such as nickel, iron, vanadium and copper, can be detrimental to the catalytic activity of the catalyst used in the cleavage process of the present disclosure, it was found, in a surprising manner, that the metal typically contained in FCC equilibrium catalysts is at a tolerable level for the process of the present disclosure. Thus, the catalyst used in the cleavage process of the present disclosure can meet at least one of the following conditions: (r1) comprising vanadium at a concentration of CV1 wt % to CV2 wt %, where CV1 can be 0.05, 0.06, 0.08, 0.10, 0.15, or 0.20; and CV2 can be 1.00, 0.95, 0.90, 0.80, 0.70, 0.60, or 0.50; (r2) comprising nickel at a concentration in a range from CN1 wt % to CN2 wt %, where CN1 can be 0.01, 0.02, 0.04, 0.05, 0.06, 0.08, 0.10, 0.15, or 0.20, and CN2 can be 0.50, 0.45, 0.40, 0.35, 0.30, or 0.25; and (r3) comprising iron at a concentration of CI1 wt % to CI2 wt %, where CI1 can be 0.05, 0.06, 0.08, 0.10, 0.15, or 0.20; and CI2 can be 1.00, 0.95, 0.90, 0.80, 0.70, 0.60, or 0.50. The catalyst may meet at least two of the requirements (r1), (r2), and (r3) above in certain examples. The catalyst may desirably meet all requirements (r1), (r2), and (r3) in other examples.

In the cleavage process of the present disclosure, the particles of the catalyst may have an average size in a range from Dp1 μm to Dp2 μm, where Dp1 can be 10, 15, 20, 25, 30, 35, 40, 45, 50, 55, 60, 65, or 70, and Dp2 can be 200, 180, 160, 150, 140, 120, 100, 90, or 80. Where the catalyst is placed in the cleavage feed to form a slurry, and the catalyst particles are filtered from the slurry and recycled in the slurry phase reaction, it is highly desired that the catalyst particles have an average particle size of at least 20 μm due to the difficulty of filtration if substantial amount of particles with size lower than 20 μm are present.

In the cleavage process of the present disclosure, at least 50%, such as at least 55%, or at least 60%, or at least 70%, or even at least 80%, by number of particles, can have a size in a range from 40 μm to 150 μm, such as in the range from 50 μm to 100 μm.

It is highly desirable that at least a portion of the catalyst particles used in the cleavage processes of the present disclosure, especially those used in a slurry process, have a spheroidal or spherical shape. Spheroidal/spherical particles are advantageous in that they reduce the friction between the particles, hence the attrition and the formation of fine particles having a size lower than 20 μm. Thus, at least 50%, such as at least 60%, or at least 70%, or at least 80%, or even at least 90%, by number of the particles, can be spheroidal and/or spherical in shape.

Catalyst particles having a spheroidal/spherical shape can be advantageously made by a spray drying process, where the solid components of the catalyst, including the FAU-type molecular sieve, the oxide binder and the clay are mixed with water optionally along with other materials, such as organic additives, to form a slurry, which is then spray dried to obtain spheroidal/spherical particles with the desired size. The particles may subsequently be calcined at a high temperature in an O$_2$-containing atmosphere, such as in a range of from 400° C. to 1000° C. for a period of at least 5 minutes, such as at least 10 minutes, or at least 30 minutes, 1 hour, 2 hours, 3 hours, 5 hours, 6 hours, 8 hours, 10 hours, 12 hours, 14 hours, 15 hours, 16 hours, 18 hours, or even at least 20 hours, to obtain the catalyst particles with the desired strength essentially free of organic matters.

The catalyst used in the cleavage process of the present disclosure desirably has a $SiO_2$ to $Al_2O_3$ ratio in a range from Rsa1 to Rsa2, where Rsa1 can be 5, 8, 10, 15, 20, 25, 30, 35, 40, 45, 50, 55, 60, 65, 70, 75, 80, 85, 90, 95, or 100; and Rsa2 can be 900, 850, 800, 750, 700, 650, 600, 550, 500, 450, 400, 350, 300, 250, 200, 150, 120, or even 100, to the extent Rsa1<Rsa2.

The cleavage reaction can be conducted using a FAU-type molecular sieve catalyst having a unit cell size of less than or equal to 24.68 Å and the reaction has a cyclohexylbenzene hydroperoxide conversion of greater than 30%, a phenol selectivity of greater than 60%, and a cyclohexanone selectivity of greater than 27%.

The cleavage reaction can be conducted using a FAU-type molecular sieve catalyst having a unit cell size of less than or equal to 24.35 Å and the reaction can have a cyclohexylbenzene hydroperoxide conversion of equal to or greater than 80%, a phenol selectivity of equal to or greater than 80%, and a cyclohexanone selectivity of equal to or greater than 80%.

The cleavage reaction can be conducted under conditions including a temperature in a range from Tr1° C. to Tr2° C., where Tr1 can be 20, 25, 30, 35, 40, 45, 50, 55, 60, 65, 70, 75, or 80, and Tr2 can be 200, 190, 180, 170, 160, 150, 140, 130, 120, 110, 100, 90, or even 80, to the extent Tr1<Tr2. It is highly desirable that the cleavage reaction is conducted under conditions such that the reaction medium is predominantly in the liquid phase.

The cleavage reaction of the present disclosure may be conducted under an absolute pressure of from Pr1 kPa to Pr2 kPa, where Pr1 can be 50, 60, 80, 100, 120, 140, 150, 160, 180, 200, 220, 240, 250, 260, 280, 300, 350, or even 400, and Pr2 can be 2000, 1800, 1600, 1500, 1400, 1200, 1000, 900, 800, 700, 600, 500, or even 400, to the extent Pr1<Pr2.

The weight hourly space velocity of the cleavage reaction may be in a range from WHSV1 to WHSV2, where WHSV1 can be 1, 2, 3, 5, 8, 10, 15, 20, 25, 30, 40, 50, 60, 80, or even 100; and WHSV2 can be 1000, 900, 800, 700, 600, 500, 400, 300, 200, or even 100, on total feed.

The cleavage reaction of the present disclosure can be conducted in a variety of reactor configurations and in either a single reactor or in a plurality of reactors. For example, the reaction may be conducted in at least a first reactor and a second reactor connected in series, with the first reactor being operated at a temperature of about 20° C. to about 120° C. and an absolute pressure in a range from 100 kPa to 800 kPa and the second reactor being operated at a temperature of about 40° C. to about 180° C. and an absolute pressure in a range from 100 kPa to 1000 kPa. The first and second reactors may be the same or different.

The cleavage reaction can be conducted in a slurry reactor, such as a stirred tank, pump-around loop or in other suitable configuration. At least part of the cleavage reaction can be conducted in a continuous stirred tank reactor (CSTR), with the catalyst being slurried in the cleavage reaction medium. Typically, the catalyst is added in an amount in a range from 50 wppm and to 20,000 wppm of the cleavage reaction medium. Advantages for this configuration include easy heat management and flexibility to add/withdraw catalyst to maintain conversion as the catalyst deactivates. If peroxide cleavage is performed with the oxidation product containing the imide catalyst, the latter may be adsorbed on the catalyst, possibly inhibiting its performance. The imide catalyst adsorbed on the catalyst can be removed or recovered by recovering the imide-loaded catalyst from the cleavage reactor and washing this spent catalyst with a polar solvent such as acetone or cyclohexanone to recover its cleavage activity and imide adsorbing capacity (rejuvenation of the catalyst). The deactivated catalyst can be also regenerated by burning off coke in air. In case the catalyst is also used for recovery of the imide catalyst, this air-regeneration is advantageously performed after recovering the adsorbed imide catalyst. In a slurry cleavage process, the catalyst can be regenerated on various schedules. Advantageously, the reaction medium containing the catalyst and the reaction products would be continuously withdrawn from the cleavage reactor, and filtered to separate the catalyst particles from the reaction medium. The catalyst may be optionally regenerated in an external recycle loop, and then returned into the cleavage reactor. Under such operation regime, a steady state of catalyst activity can be maintained through regeneration and by continuously replacing a fraction of the recycled catalyst with fresh catalyst. In a slurry reaction process, the catalyst desirably has a durability such that at most Du wt % of the catalyst particles having a size over 20 μm are broken down to a size below 20 μm after a continuous operation of 24 hours, where Du can be 2.0, 1.8, 1.6, 1.5, 1.4, 1.2, 1.0, 0.8, 0.6, 0.5, 0.4, 0.3, 0.2, or even 0.1.

The catalyst can also be used in a fixed bed plug-flow reactor with or without first removing the imide catalyst from the cleavage feed stream. If the imide catalyst is not removed, the catalyst bed adsorbs at least a portion of it, allowing its recovery and recycle to the oxidation process. In such a process design, two or more parallel cleavage reactor trains may be deployed to enable uninterrupted processing of the peroxide feed. Thus, as the catalyst becomes saturated with the imide catalyst causing it to deactivate in one reactor train, the cleavage feed is switched to another reactor train that contains fresh or regenerated catalyst. The imide-saturated catalyst can be rejuvenated off-line by, for example, flushing with a polar solvent such as acetone or cyclohexanone. The imide catalyst recovered can be re-used for oxidation. The coke on catalyst can then also be removed by burning in air before the regenerated reactor train is returned to cleavage operation to replace the previously operating reactor train that can now be taken off-line for regeneration. This cycle then can be repeated until the catalyst in one or more reactor trains can no longer be regenerated to acceptable levels. In such cases, the exhausted catalyst can simply be replaced with a fresh charge before returning the train to cleavage operations.

The cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises cyclohexylbenzene hydroperoxide at a concentration in a range from CCHB1 to CCHB2, where CCHB1 can be 1.0, 1.5, 2.0, 2.5, 3.0, 3.5, 4.0, 4.5, 5.0, 6.0, 8.0, 10.0, 12.0, 14.0, or 15.0; and CCHB2 can be 40.0, 38.0, 36.0, 35.0, 32.0, 30.0, 28.0, 26.0, 25.0, 24.0, 22.0, or 20.0. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical induced conversion of the cyclohexylbenzene hydroperoxide to undesired products such as hexanophenone and phenylcyclohexanol.

The cleavage reaction mixture can include cyclohexylbenzene in an amount of at least 10 wt %, or at least 20 wt %, or least 30 wt %, or at least 40 wt %, or at least 50 wt %, or at least 60 wt %, or at least 65 wt %, or at least 70 wt %, or at least 80 wt %, or at least 90 wt %, based upon total weight of the cleavage reaction mixture.

The cleavage reaction using the FAU-type molecular sieve catalyst may have a cyclohexylbenzene hydroperoxide conversion, Con(CHBHP), in a range from Con(CHBHP)1 to Con(CHBHP)2, where Con(CHBHP)1 can be 30.0, 40.0, 50.0, 60.0, 70.0, 75.0, 80.0, 82.0, 84.0, 85.0, 86.0, 88.0, or 90.0, and Con(CHBHP)2 can be 100.0, 99.9, 99.5, 99.0, 98.5, 98.0, 97.5, 97.0, 96.0, 95.0, 94.0, 93.0, 92.0, or even 91.0. As used herein, "cyclohexylbenzene hydroperoxide conversion" means the amount of cyclohexylbenzene hydroperoxide converted to any product. A high conversion of at least 85.0%, or at least 88.0%, or at least 90.0%, or at least 92.0%, or at least 95.0%, or at least 98.0%, or at least 99.0%, or even at least 99.5% is highly desired because cyclohexylbenzene hydroperoxide contained in the product becomes a contaminant in the cleavage reaction mixture and treated cleavage reaction mixture, discussed below. Hydroperoxides cause undesired chemistry when decomposed under uncontrolled conditions outside the cleavage reaction, or if thermally decomposed under the conditions in a distillation column.

The cleavage reaction effluent may comprise phenol at a concentration from CPH1 wt % to CPH2 wt %, based on total weight of the cleavage reaction mixture, where CPH1 can be 1.0, 2.0, 3.0, 5.0, 8.0, 10, 12, 14, 15, 16, 18, 20, 22, 24, 25, 26, 28, or 30; and CPH2 can be 60, 55, 50, 45, 44, 42, 40, 38, 36, 35, 34, 32, 30, 28, 26, or 25, the extent CPH1<CPH2. Further, the cleavage reaction effluent may comprise cyclohexanone at a concentration from CHN1 wt % to CHN2 wt %, based on total weight of the cleavage reaction mixture, where CHN1 can be 1.0, 2.0, 3.0, 5.0, 8.0, 10, 12, 14, 15, 16, 18, 20, 22, 24, 25, 26, 28, or 30; and CHN2 can be 60, 55, 50, 45, 44, 42, 40, 38, 36, 35, 34, 32, 30, 28, 26, or 25, to the extent CHN1<CHN2.

As used herein, "phenol selectivity" is relative to the theoretical phenol selectivity based upon the amount of cyclohexylbenzene hydroperoxide converted. "Cyclohexanone selectivity" is relative to the theoretical cyclohexanone selectivity based upon the amount of cyclohexylbenzene hydroperoxide converted. Thus:

Sel(Phen)=$n$(Phen)/$n$(CHBHP)*100%,

Sel(CHXN)=$n$(CHXN)/$n$(CHBHP)*100%, where Sel(phen) and Sel(CHXN) are phenol selectivity and cyclohexanone selectivity, respectively, n(Phen) and n(CHXN) are the quantities in moles of phenol and cyclohexanone produced in the reaction, and n(CHBHP) is the quantity of cyclohexylbenzene hydroperoxide consumed in the reaction in moles. Sel(Phen) can range from Sel(Phen)1 to Sel(Phen)2, and Sel(CHXN) can range from Sel(CHXN)1 to Sel(CHXN)2, where Sel(Phen)1 and Sel(CHXN)1 can be independently 50.0, 55.0, 60.0, 65.0, 70.0, 72.0, 74.0, 75.0, 76.0, 78.0, or 80.0; and Sel(Phen)2 and Sel(CHXN)2 can be independently 99.0, 98.0, 96.0, 95.0, 94.0, 92.0, 90.0, 88.0, 86.0, 85.0, 84.0, 82.0, or 80.0, to the extent Sel(Phen)1<Sel(Phen)2, and Sel(CHXN)1<Sel(CHXN)2.

It was found that, when sulfuric acid is used as the catalyst, the cleavage process of cyclohexylbenzene hydroperoxide tends to produce less cyclohexanone than phenol, resulting in a non-negligible net penalty of cyclohexanone selectivity. Without intending to be bound by a particular theory, it is believed that such penalty is due to side reactions caused by the use of sulfuric acid as the catalyst. Due to the use of solid acid catalyst, the process of the present disclosure advantageously results in a selectivity of phenol substantially the same as cyclohexanone. Thus, the phenol selectivity of the cleavage reaction can be Sel(Phen), and the cyclohexanone selectivity of the cleavage reaction can be Sel(CHXN), R1≤| (Sel(Phen)−Sel(CHXN))|/Sel(Phen)≤R2, where R1 and R2 can be 0.10, 0.09, 0.08, 0.07, 0.06, 0.05, 0.04, 0.03, 0.02, or even 0.01, as long as R1<R2.

The cleavage reaction mixture may further comprise at least 0.1 wt % and no greater than 10 wt %, or at least 0.5 wt % and no greater than 7 wt %, or at least 1 wt % and no greater than 5 wt %, or at least 1.5 wt % and no greater than 3 wt % of any one or combination of contaminant by-products based on the total weight of the cleavage reaction mixture.

As used herein, a "contaminant" or a "contaminant byproduct" may include any unwanted hydrocarbon or oxygenated hydrocarbon component in the cleavage reaction mixture that is anything other than phenol, cyclohexanone, and cyclohexylbenzene. They are unwanted because their presence indicates a decreased yield of desired product phenol and cyclohexanone from cyclohexylbenzene, or they cause difficulties in the separation and purification of phenol, cyclohexanone or unconverted cyclohexylbenzene, or some combination thereof. A contaminant in the cleavage reaction mixture, or the neutralized cleavage mixture, or any portion thereof may have been produced, or may have been contained in the feed comprising cyclohexylbenzene undergoing oxidation. For example, a contaminant may be present in the cleavage reaction mixture as a result of one or more of: (i) it was included with the cyclohexylbenzene (e.g., as a byproduct of production using hydroalkylation or alkylation); (ii) it was produced in oxidation of the feed comprising cyclohexylbenzene, and potentially the oxidation of an oxidizable component from (i); and/or (iii) it was produced in the cleavage reaction of at least a portion of the oxidation composition from (ii).

The cleavage reactor can be operated to transport a portion of the contents through a cooling device and return the cooled portion to the cleavage reactor, thereby managing the exothermicity of the cleavage reaction. Alternatively, the reactor may be operated adiabatically. Cooling coils operating within the cleavage reactor(s) may be used to remove at least part of the heat generated.

Contaminant Treatment

As discussed above, the cleavage reaction mixture may comprise one or more contaminants. The processes may further comprise contacting at least a portion of a contaminant with an acidic material to convert at least a portion of the contaminant to a converted contaminant, thereby producing a modified reaction mixture. Detailed description of the contaminant treatment process can be found in, e.g., International Publication WO2012/036822A1, the relevant content of which is incorporated herein by reference in its entirety.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, ϵ-caprolactam, adipic acid, and/or plasticizers.

The following examples demonstrate cleavage of CHBHP using spray dried catalysts, both in slurry batch and fixed-bed operations.

Example 1

Oxidation of Cyclohexylbenzene

An amount of 631 g of cyclohexylbenzene (CHB, available from TCI America, Inc.) was added to a 1-liter four-necked glass flask, toward which 0.6702 g of NHPI (available from TCI America, Inc.) was added. The flask was then fitted with a reflux condenser, a mechanical stirrer, a gas sparger, and a thermometer. An air flow of 250 cm$^3$/min was bubbled through the liquid via the gas sparger; and the content was heated at 110° C. with stirring (560 rpm) for 6 hr. The flask was then allowed to cool down to room temperature and the oxidation product recovered. GC analysis indicated the product contained 17.9% CHBHP.

Example 2

Cleavage of CHBHP (about 3 wt % CHBHP) Using Sulfuric Acid in Batch Operation (Comparative)

An amount of 30 g mixture of CHBHP/CHB/phenol/cyclohexanone (about 3/81/8/8 weight ratio) and dodecane (internal standard) was charged to a 50-mL jacketed glass reactor with a circulating temperature bath. The bath was set to desired temperature and the reactor content was allowed to equilibrate. Once the temperature stabilized, a GC sample was taken for the hot feed. Desired amount of concentrated sulfuric acid (96%, triple-distilled, available from Aldrich) was then added via a micro-syringe. After a brief reaction exotherm, as indicated by the temperature rise inside the reactor, a 1-mL aliquot was taken at certain time intervals and neutralized with a stoichiometric amount of dihexylamine. The samples generated were analyzed by GC and the results are shown in Table 1.

Example 3

Cleavage of CHBHP (about 3 wt % CHBHP) Using FCC Equilibrium Catalysts in Batch Operation (Invention)

A set of four catalyst FCC samples, 3.1, 3.2, 3.3, and 3.4, were tested. All four samples were equilibrium catalyst containing a mixture of fresh, non-deactivated FCC catalyst particles and deactivated FCC catalyst particles. All samples were first calcined at 600° C. in air for 2 hours prior to being tested below.

An amount of 5 g mixture of CHBHP/CHB/phenol/cyclohexanone (about 3/81/8/8 weight ratio) and dodecane (internal standard) was charged to a 10-mL jacketed glass reactor with a circulating temperature bath. The bath was set to desired temperature and the reactor content was allowed to equilibrate. Once the temperature stabilizes, a GC sample was taken for the hot feed. An amount of 0.2 g catalyst (4 wt % relative to feed) described in the preceding paragraph was then added to the mixture. After 10 min of reaction, a 1-mL aliquot was taken and the solid filtered. The samples generated were analyzed by GC and the results are shown in Table 1.

TABLE 1

Cleavage of CHBHP (about 3 wt % CHBHP) using sulfuric acid and FCC equilibrium catalysts in batch mode

|  | Catalyst Sample ID | | | | |
| --- | --- | --- | --- | --- | --- |
|  | 3.1 | 3.2 | 3.3 | 3.4 | H$_2$SO$_4$ |
| Collidine Uptake (μmol/g) | 27.4 | 59.6 | 47.1 | 50.7 | — |
| N-Hexane Uptake (mg/g) | 15.8 | 24.3 | 23.6 | 27.9 | — |
| Maximal TPAD Temperature (° C.) | 285 | 288 | 285 | 292 | — |
| BET total SA (m$^2$/g) | 121 | 161 | 163 | 218 | — |
| V (wt %) | 0.369 | 0.148 | 0.216 | 0.105 | — |
| Ni (wt %) | 0.136 | 0.171 | 0.144 | 0.034 | — |
| Fe (wt %) | 0.455 | 0.314 | 0.558 | 0.531 | — |
| Reaction Temperature (° C.) | 55 | 55 | 55 | 55 | 60 |
| Reaction Time (min) | 10 | 10 | 10 | 10 | 4 |
| CHBHP Conversion (%) | 22 | 49 | 68 | 61 | 99 |
| Phenol Selectivity (%) | 92 | 85 | 87.6 | 84.7 | 95 |
| Cyclohexanone Selectivity (%) | 90.6 | 85.6 | 87.6 | 84 | 86 |

For sulfuric acid catalyzed cleavage, a debit in cyclohexanone selectivity is seen (86% for cyclohexanone vs. 95% for phenol as shown in Example 2). Surprisingly, no cyclohexanone selectivity debit is seen with FCC equilibrium catalysts. All four catalyst samples, 3.1, 3.2, 3.3, and 3.4 contained vanadium, nickel and iron at various amounts as indicated in Table 1 above. Yet, they all exhibited satisfactory cyclohexylbenzene hydroperoxide conversion, phenol selectivity and cyclohexanone selectivity.

Example 4

Cleavage of CHBHP Using Experimental FCC Catalyst in Fixed-Bed Operation (Invention)

The CHBHP from Example 1 was diluted with CHB and dodecane (internal standard) to obtain a feed containing about 4 wt % CHBHP. An amount of 2 g of spray dried experimental FCC catalyst was diluted with quartz chips to 5 cm$^3$ volume and loaded into the center zone of a ⅜" tubular reactor. The catalyst was first dried with flowing N$_2$ at 200° C. and then temperature cooled down to 50° C. The CHBHP feed was fed to the reactor via an ISCO pump at a liquid pressure of 100 psig. Cleavage product was collected and analyzed by GC. The conversion for CHBHP is shown in FIG. 1 in zone 101. The catalyst deactivated with time.

To regenerate the catalyst, the reactor was first flushed with hexanes, then purged with flowing N$_2$ (100 cm$^3$/min) at 50° C. The flowing N$_2$ was then switched to air (100 cm$^3$/min) and the temperature ramped to 550° C. The reactor was held at 550° C. for 2 h under flowing air. The reactor was then cooled down to 50° C., the gas turned off and the CHBHP feed was resumed (100 psig, 689 kPa, liquid pressure). The regeneration was done twice (shown as zones 103 and 105 separated by vertical dotted lines in FIG. 1); and the conversion clearly recovers after regeneration. Selectivities for the fresh and regenerated catalyst are shown in Table 2.

Similar to the slurry phase reaction, no or very little debit in cyclohexanone selectivity is seen in fixed-bed operation using spray dried experimental FCC catalyst. In addition, catalyst regenerability has been shown in this example.

TABLE 2

Selectivities to phenol and cyclohexanone for spray dried
FCC catalyst before and after regeneration
(at comparable conversions about 80-90%)

|  | Phenol selectivity (%) | Cyclohexanone selectivity (%) |
|---|---|---|
| Fresh | 85.3 | 87.9 |
| First regeneration | 87.9 | 85.4 |
| Second regeneration | 81.6 | 80.5 |

While the present invention has been described and illustrated by reference to particular embodiments, those of ordinary skill in the art will appreciate that the invention lends itself to variations not necessarily illustrated herein. For this reason, reference should be made solely to the appended claims for purposes of determining the true scope of the present invention.

Contents of all references cited herein are incorporated by reference in their entirety.

Non-limiting aspects and/or embodiments of the present disclosure include:

E1. A process for making phenol and/or cyclohexanone, the process comprising:
(A) providing a feed comprising cyclohexylbenzene hydroperoxide;
(B) contacting the feed with a catalyst under cleavage reaction conditions effective to produce a cleavage effluent comprising phenol and cyclohexanone, the catalyst having a collidine uptake of at least 20 μmol per gram of the catalyst and comprising (i) an aluminosilicate molecular sieve of the FAU-type; (ii) an oxide binder; and (iii) a clay.

E2. The process of E1, wherein the catalyst in step (B) comprises the molecular sieve of the FAU-type in a range from 20 wt % to 60 wt %, an oxide binder in a range from 10 wt % to 40 wt %, and clay in a range from 5 wt % to 30 wt %, all percentages based on the total weight of the catalyst.

E3. The process of E1 or E2, wherein the catalyst has an n-hexane uptake of at least 20 mg per gram of the catalyst.

E4. The process of any of E1 to E3, wherein the catalyst has a maximal TPAD temperature of at least 260.

E5. The process of any of E1 to E4, wherein the molecular sieve of the FAU-type in the catalyst in step (B) has a unit cell size in a range from 24.24 to 24.68.

E6. The process of any of E1 to E5, wherein the catalyst comprises a FCC catalyst.

E7. The process of E6, wherein the catalyst comprises a spent FCC catalyst.

E8. The process of E7, wherein before contacting the feed with the catalyst, the catalyst is calcined at a temperature in a range from 500° C. to 1000° C. in an $O_2$-containing atmosphere for a period of at least 5 minutes.

E9. The process of any of E1 to E8, wherein the catalyst meets at least one of the following requirements:
(r1) comprising vanadium in a range from 0.05 wt % to 1.0 wt %;
(r2) comprising nickel in a range from 0.01 wt % to 0.5 wt %; and
(r3) comprising iron in a range from 0.05 wt % to 1.0 wt %.

E10. The process of E9, wherein the catalyst meets at least two of the requirements (r1), (r2), and (r3).

E11. The process of E10, wherein the catalyst meets all three requirements of (r1), (r2), and (r3).

E12. The process of any of E1 to E11, wherein the catalyst in step (B) comprises a plurality of particles having an average size in a range from 20 μm to 200 μm, such as from 40 μm to 150 μm, or from 50 to 100 μm.

E13. The process of E12, wherein at least 50% of the plurality of particles are spheroidal and/or spherical, the percentages based on the total number of the particles.

E14. The process of any of E1 to E13, wherein at least 50% of the particles have a size in a range from 40 μm to 150 μm, such as from 50 to 100 μm.

E15. The process of any of E1 to E14, wherein the catalyst is made by a process comprising a spray drying step.

E16. The process of any of E1 to E15, wherein the FAU-type molecular sieve has a $SiO_2$ to $Al_2O_3$ molar ratio from 5 to 900, in certain embodiments from 30 to 200, in certain other embodiments from 60 to 100.

E17. The process of any of E1 to E16, wherein step (B) comprises:
(B-I) mixing the feed with a plurality of particles of the catalyst in a cleavage reactor to obtain a slurry; and
(B-II) separating at least a portion of the slurry to obtain the cleavage effluent and a particle stream comprising the catalyst.

E18. The process of E17, wherein step (B) further comprises:
(B-III) recycling at least a portion of the particle stream into step (B-I) as a portion of the source of the plurality of particles of the catalyst.

E19. The process of E17 or E18, wherein the catalyst has a durability such that at most 2.0 wt % of the catalyst particles having a size over 20 μm are broken down to a size below 20 μm after a continuous operation of 24 hours.

E20. The process of E19, wherein the catalyst has a durability such that the at most 1.0 wt % of the catalyst particles having a size over 20 μm are broken down to a size below 20 μm after a continuous operation of 24 hours.

E21. The process of any of E17 to E20, wherein step (B) further comprises:
(B-IV) regenerating at least a portion of the catalyst in the particle stream.

E22. The process of E21, wherein step (B) further comprises:
(B-V) recycling at least a portion of the regenerated catalyst to step (B-I).

E23. The process of E21 or E22, wherein step (B-IV) comprises heating the catalyst at a temperature in a range from 400° C. to 800° C. in an $O_2$-containing atmosphere.

E24. The process of any of E1 to E23, wherein in step (B), the phenol selectivity is Sel(Phen), and the cyclohexanone selectivity is Sel(CHXN), where R1≤|(Sel(Phen)−Sel(CHXN))|/Sel(Phen)≤R2, where R1 and R2 in various embodiments can be 0.10, 0.09, 0.08, 0.07, 0.06, 0.05, 0.04, 0.03, 0.02, or even 0.01, as long as R1<R2.

E25. The process of any of E1 to E24, wherein the feed in step (A) is provided by a process comprising:
(A-I) contacting benzene with cyclohexene in the presence of an alkylation catalyst under alkylation conditions effective to produce an alkylation reaction effluent comprising cyclohexylbenzene;
(A-II) contacting at least a portion of the cyclohexylbenzene with an $O_2$-containing atmosphere under oxidation conditions effective to produce an oxidation reaction effluent comprising cyclohexylbenzene hydroperoxide; and
(A-III) obtaining the feed from the oxidation reaction effluent.

E26. The process of E25, wherein step (A-I) comprises contacting benzene with hydrogen in the presence of a hydroalkylation catalyst under a hydroalkylation condition effective to produce the alkylation reaction effluent.

E27. The process of any of E1 to E26, wherein the catalyst in the contacting step (B) is a fluid cracking catalyst.

E28. The process of E27, wherein the catalyst in the contacting step (B) is an equilibrated fluid cracking catalyst.

E29. The process of any of E1 to E28, wherein in step (B), the amount of the catalyst used is in a range from 0.1 wt % to 20 wt %, based on the total weight of the feed.

The invention claimed is:

1. A process for making phenol and/or cyclohexanone, the process comprising:
   (A) providing a feed comprising cyclohexylbenzene hydroperoxide;
   (B) contacting the feed with a catalyst under cleavage reaction conditions effective to produce a cleavage effluent comprising phenol and cyclohexanone, the catalyst having a collidine uptake of at least 20 µmol per gram of the catalyst and comprising an aluminosilicate molecular sieve of the FAU-type, an oxide binder, and a clay.

2. The process of claim 1, wherein the catalyst comprises the molecular sieve of the FAU-type in a range from 20 wt % to 60 wt %, the oxide binder in a range from 10 wt % to 40 wt %, and the clay in a range from 5 wt % to 30 wt %, all percentages based on the total weight of the catalyst.

3. The process of claim 1, wherein the catalyst has an n-hexane uptake of at least 20 mg per gram of the catalyst.

4. The process of claim 1, wherein the catalyst has a maximal TPAD temperature of at least 260° C.

5. The process of claim 1, wherein the molecular sieve of the FAU-type in the catalyst has a unit cell size in a range from 24.24 to 24.68.

6. The process of claim 1, wherein the catalyst comprises a FCC catalyst.

7. The process of claim 6, wherein the catalyst comprises a spent FCC catalyst.

8. The process of claim 7, wherein before contacting the feed with the catalyst, the catalyst is calcined at a temperature in a range from 500° C. to 1000° C. in an $O_2$-containing atmosphere for a period of at least 5 minutes.

9. The process of claim 1, wherein the catalyst meets at least one of the following requirements:
   (r1) comprising vanadium in a range from 0.05 wt % to 1.0 wt %,
   (r2) comprising nickel in a range from 0.01 wt % to 0.5 wt %, and
   (r3) comprising iron in a range from 0.05 wt % to 1.0 wt %, where all percentages are based on the total weight of the catalyst.

10. The process of claim 1, wherein the catalyst comprises a plurality of particles having an average size in a range from 20 µm to 200 µm.

11. The process of claim 10, wherein at least 50% of the plurality of particles are spheroidal and/or spherical, the percentages based on the total number of the particles.

12. The process of claim 1, wherein the catalyst is made by a process comprising a spray drying step.

13. The process of claim 1, wherein the FAU-type molecular sieve has a $SiO_2$ to $Al_2O_3$ molar ratio in a range from 5 to 900.

14. The process of claim 1, wherein step (B) comprises:
   (B-I) mixing the feed with a plurality of particles of the catalyst in a cleavage reactor to obtain a slurry; and
   (B-II) separating at least a portion of the slurry to obtain the cleavage effluent and a particle stream comprising the catalyst.

15. The process of claim 14, wherein step (B) further comprises:
   (B-III) recycling at least a portion of the particle stream into step (B-I) as a portion of the source of the plurality of particles of the catalyst.

16. The process of claim 14, wherein the catalyst has a durability such that at most 2.0 wt % of the catalyst particles having a size over 20 µm are broken down to a size below 20 µm after a continuous operation of 24 hours.

17. The process of claim 14, wherein step (B) further comprises:
   (B-IV) regenerating at least a portion of the catalyst in the particle stream.

18. The process of claim 17, wherein step (B) further comprises:
   (B-V) recycling at least a portion of the regenerated catalyst to step (B-I).

19. The process of claim 17, wherein step (B-IV) comprises heating the catalyst at a temperature in a range from 400° C. to 800° C. in an $O_2$-containing atmosphere.

20. The process of claim 1, wherein in step (B), the phenol selectivity is Sel(Phen), and the cyclohexanone selectivity is Sel(CHXN), where $0.01 \leq |(Sel(Phen) - Sel(CHXN))|/Sel(Phen) \leq 0.10$.

21. The process of claim 1, wherein step (A) comprises:
   (A-I) contacting benzene with cyclohexene in the presence of an alkylation catalyst under alkylation conditions effective to produce an alkylation reaction effluent comprising cyclohexylbenzene;
   (A-II) contacting at least a portion of the cyclohexylbenzene with an $O_2$-containing atmosphere under oxidation conditions effective to produce an oxidation reaction effluent comprising cyclohexylbenzene hydroperoxide; and
   (A-III) obtaining the feed from the oxidation reaction effluent.

22. The process of claim 21, wherein step (A-I) comprises contacting benzene with hydrogen in the presence of a hydroalkylation catalyst under a hydroalkylation condition effective to produce the alkylation reaction effluent.

23. The process of claim 1, wherein in step (B), the amount of the catalyst is in a range from 0.1 wt % to 20 wt % based on the weight of the feed.

* * * * *